United States Patent [19]

Wolf et al.

[11] Patent Number: 4,968,695
[45] Date of Patent: Nov. 6, 1990

[54] SUBSTITUTED NITROALKENES AND USE AS PESTICIDES AND INSECTICIDES

[75] Inventors: Hilmar Wolf, Langenfeld; Benedikt Becker, Mettmann; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 192,445

[22] Filed: May 11, 1988

[30] Foreign Application Priority Data

May 27, 1987 [DE] Fed. Rep. of Germany ....... 3717837

[51] Int. Cl.$^5$ .................... A61K 31/44; C07F 7/02; C07F 9/06; C07D 213/04
[52] U.S. Cl. ........................... 514/63; 514/89; 514/333; 514/340; 514/341; 514/342; 546/14; 546/22; 546/24; 546/256; 546/275; 546/278; 546/280
[58] Field of Search ............... 546/14, 22, 24, 275, 546/278, 280, 256; 514/340, 341, 342, 333, 63, 89

[56] References Cited

U.S. PATENT DOCUMENTS 3,993,648 11/1976 Powell .................................. 544/53

Primary Examiner—Mary C. Lee
Assistant Examiner—J. Richter
Attorney, Agent, or Firm—Sprung Horn Kramer & Woods

[57] ABSTRACT

Pest-combating agents, in particular as insecticides which substituted nitroalkenes of the formula

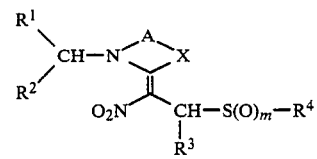

in which
 m represents 0, 1 or 2,
 A represents alkanediyl,
 $R^1$ represents an optionally substituted five-or six-membered heterocyclic grouping,
 $R^2$ represents hydrogen or alkyl,
 $R^3$ represents hydrogen or optionally substituted alkyl, alkenyl, alkinyl, benzyl, furyl, furylmethyl, thenyl, thienyl or pyridyl,
 $R^4$ represents optionally substituted phenyl, pyrimidinyl, imidazolyl or triazolyl and
 X represents oxygen, sulphur or the grouping N—$R^5$,
wherein
 $R^5$ represents hydrogen, optionally substituted alkyl, alkenyl, alkinyl, or benzyl, formyl, or optionally substituted alkylcarbonyl, cycloalkylcarbonyl, alkenylcarbonyl, phenylcarbonyl or naphthylcarbonyl.

7 Claims, No Drawings

SUBSTITUTED NITROALKENES AND USE AS PESTICIDES AND INSECTICIDES

The present invention relates to new substituted nitroalkenes, a process for their preparation and their use in pest-combating agents, in particular as insecticides.

It has already been disclosed that certain organic nitro compounds such as, for example, 2-nitromethylene-2H-tetrahydro-1,3-thiazine exhibit insecticidal properties (U.S. Pat. No. 3,993,648).

New substituted nitroalkenes of the general formula (I)

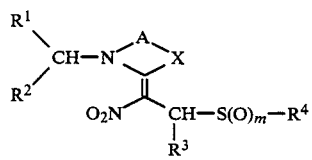

in which
m represents the numbers 0, 1 or 2,
A represents alkanediyl,
$R^1$ represents a five- or six-membered heterocyclic grouping which contains 1, 2, 3 or 4 nitrogen atoms and/or one or two oxygen or sulphur atoms as heteroatom ring members—the number of heteroatoms being 1, 2, 3 or 4—and which is optionally substituted by halogen, cyano, nitro, alkyl, halogenoalkyl, alkenyl, halogenoalkenyl, alkinyl, alkoxy, halogenoalkoxy, alkenyloxy, halogenoalkenyloxy, alkinyloxy, alkylthio, haloqenoalkylthio, alkenylthio, halocenoalkenylthio, alkinylthio, alkylsulphinyl, halogenoalkylsulphinyl, alkylsulphonyl, halogenoalkylsulphonyl, amino, alkylamino, dialkylamino, aryl, aryloxy, arylthio, arylamino, aralkyl, formylamino, alkylcarbonylamino, formyl, carbamoyl, alkylcarbonyl and/or alkoxycarbonyl,
$R^2$ represents hydrogen or alkyl,
$R^3$ represents hydrogen, alkyl (which is optionally substituted by halogen, cyano, alkoxy or alkylthio), alkenyl (which is optionally substituted by halogen or phenyl), alkinyl, phenyl (which is optionally substituted by halogen, cyano, nitro, alkyl, halogenoalkyl, alkoxy, halogenoalkoxy, alkylthio, halogenoalkylthio, alkylsulphinyl, alkylsulphonyl, halogenoalkylsulphonyl, dialkylamino or alkoxycarbonyl), benzyl (which is optionally substituted by halogen, cyano, nitro, alkyl, halogenoalkyl or alkoxycarbonyl), furyl, furylmethyl, or pyridyl (which are optionally substituted by halogen or alkyl),
$R^4$ represents phenyl (which is optionally substituted by halogen, cyano, nitro, alkyl, halogenoalkyl, alkoxy, halogenoalkoxy, alkylthio, halogenoalkylthio, amino, alkylamino, dialkylamino or alkoxycarbonyl), naphthyl (which is optionally substituted by halogen, cyano, nitro, alkyl or amino), pyridinyl (which is optionally substituted by halogen or alkyl), pyrimidinyl (which is optionally substituted by halogen or alkyl), imidazolyl or triazolyl and
X represents oxygen, sulphur or the grouping N—$R^5$, wherein $R^5$ represents hydrogen, alkyl (which is optionally substituted by halogen, cyano, alkoxy, alkylthio, dialkylamino, trialkylsilyl, alkoxycarbonyl, carboxyl, carbamoyl, alkylaminocarbonyl, dialkylaminocarbonyl or by the radical $R^1$, $R^1$ possessing the abovementioned meaning), alkenyl (which is optionally substituted by halogen), alkinyl, benzyl which is optionally substituted by halogen, cyano, nitro, alkyl, halogenoalkyl, alkoxy or alkoxycarbonyl), formyl, alkylcarbonyl (which is optionally substituted by halogen, cyano, phenyl, phenoxy or alkoxy), cycloalkylcarbonyl (which is optionally substituted by halogen and/or alkyl), alkenylcarbonyl (which is optionally substituted by halogen), phenylcarbonyl or naphthylcarbonyl (which are optionally substituted by halogen, alkyl, halogenoalkyl, cyano, nitro, alkoxy and/or alkoxycarbonyl), alkoxycarbonyl, benzyloxycarbonyl, phenoxycarbonyl, alkylthiocarbonyl, benzylthiocarbonyl, phenylthiocarbonyl, alkylaminocarbonyl, dialkylaminocarbonyl, phenylaminocarbonyl (which is optionally substituted by halogen, cyano, nitro, alkyl, halogenoalkyl, alkoxy, halogenoalkoxy, alkylthio, halogenoalkylthio or alkoxycarbonyl), benzoylaminocarbonyl (which is optionally substituted by halogen, alkyl or halogenoalkyl), phenylsulphonylaminocarbonyl (which is optionally substituted by halogen, alkyl, halogenoalkyl, alkoxy, halogenoalkoxy or alkoxycarbonyl), alkylthio (which is optionally substituted by halogen), phenylthio (which is optionally substituted by halogen, nitro or alkyl), alkylsulphinyl, alkylsulphonyl (which is optionally substituted by halogen), phenylsulphinyl (which is optionally substituted by halogen, nitro or alkyl), phenylsulphonyl or naphthylsulphonyl (which are optionally substituted by halogen, cyano, nitro, alkyl, halogenoalkyl, alkoxy, halogenoalkoxy and/or alkoxycarbonyl), dialkyl(thio)phosphoryl, alkylalkoxy-(thio)phosphoryl or dialkoxy(thio)phosphoryl, have now been found.

The present invention also relates to the individual possible Z and E isomers of the formula (I) above and the formula (I') below—wherein m, A, $R^1$, $R^2$, $R^3$, $R^4$ and X have the abovementioned meanings—and the possible optical isomers—provided that $R^2$ and/or $R^3$ are different from hydrogen—and also any mixtures of all possible isomers.

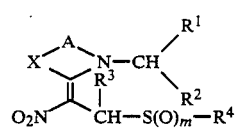

In the following, the simplifying formulation "compounds of the formula (I)" in each case relates to the compounds outlined by the formulae (I) and (I').

The new substituted nitroalkenes of the general formula (I) are obtained when nitroalkenes of the general formula (II)

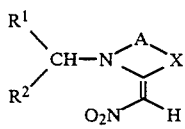
(II)

in which

A, R$^1$, R$^2$ and X have the abovementioned meanings—or the isomers of the corresponding configuration (Z or E) or mixtures of the Z and E isomers—are reacted with aldehydes of the general formula (III)

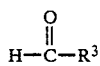
(III)

in which

R$^3$ has the abovementioned meaning, and with mercapto compounds of the general formula (IV)

$$HS-R^4 \quad (IV)$$

in which

R$^4$ has the abovementioned meaning, if appropriate in the presence of an acid and if appropriate in the presence of a diluent, and the resultant compounds of the formula (I) in which m represents the number 0 and A, R$^1$, R$^2$, R$^3$, R$^4$ and X have the abovementioned meanings, are converted, if desired, by customary oxidation methods into corresponding compounds of the formula (I) in which m then represents the numbers 1 or 2 and A, R$^1$, R$^2$, R$^3$, R$^4$ and X have the abovementioned meanings.

Further possible preparation methods for the compounds of the general formula (I) according to the invention, in which m, R$^1$, R$^2$, R$^3$, R$^4$ and X have the abovementioned meanings are shown schematically below:

(a) reaction of halogen compounds of the formula (V) (Y=halogen) with nitroalkenes of the formula (VI), if appropriate in the presence of an acid acceptor such as, for example, potassium carbonate, and if appropriate in the presence of a diluent such as, for example, acetone, acetonitrile or dimethylformamide, at temperatures between 10° C. and 100° C.:

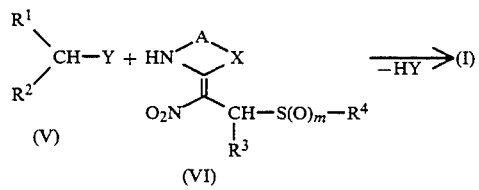

(b) reaction of nitroalkenes of the formula (Ia) (X=NH) with halogen compounds of the formula (VII) (Z=halogen), if appropriate in the presence of an acid acceptor such as, for example, potassium carbonate and if appropriate in the presence of a diluent such as, for example, acetone, acetonitrile or dimethylformamide, at temperatures between 10° C. and 100° C.:

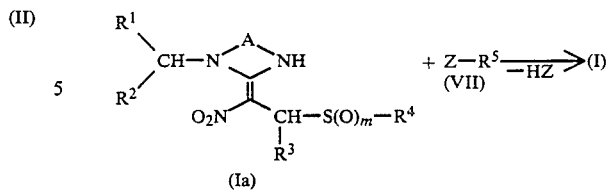

(c) reaction of amines of the formula (VIII) with 1,1-bis-methylthio-3-nitro-alkenes of the formula (IX), if appropriate in the presence of a diluent such as, for example, toluene, xylene or dioxane, at temperatures between 10° C. and 150° C.:

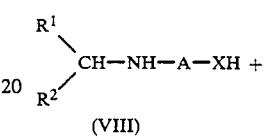

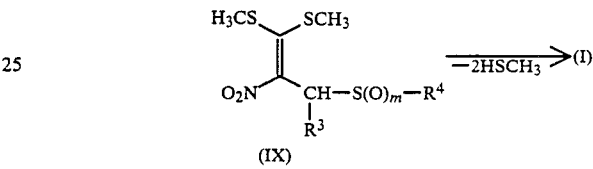

The new substituted nitroalkenes of the general formula (I) are distinguished by a high insecticidal activity. Surprisingly, the compounds of the formula (I) according to the invention show a considerably stronger insecticidal action than organic nitro compounds which are comparable in structure and activity profile, such as, for example, 2-nitromethylene-2H-tetrahydro-1,3-thiazine.

The invention preferably relates to compounds of the formula (I) in which m represents the numbers 0, 1 or 2, A represents C$_2$-C$_5$-alkanediyl, R$^1$ represents a five- or six-membered heterocyclic grouping from the series comprising furyl, thienyl, pyrrolyl, pyrazolyl, imidazolyl, 1,2,3- or 1,2,4-triazolyl, oxazolyl, isoxazolyl, 1,2,4- or 1,3,4-oxadiazolyl, thiazolyl, isothiazolyl, 1,2,3-, 1,2,4-, 1,2,5- or 1,3,4-thiadiazolyl, pyridyl, pyridazinyl, pyrimidinyl and pyrazolyl, each of which is optionally substituted by fluorine, chlorine, bromine, iodine, cyano, nitro, C$_1$-C$_4$-alkyl (which is optionally substituted by fluorine and/or chlorine), C$_2$-C$_4$-alkenyl (which is optionally substituted by fluorine and/or chlorine), C$_2$-C$_4$-alkinyl, C$_1$-C$_4$-alkoxy (which is optionally substituted by fluorine and/or chlorine), C$_3$-C$_4$-alkenyloxy (which is optionally substituted by fluorine and/or chlorine), C$_3$-C$_4$-alkinyloxy, C$_1$-C$_4$-alkylthio (which is optionally substituted by fluorine and/or chlorine), C$_3$-C$_4$-alkenylthio (which is optionally substituted by fluorine and/or chlorine), C$_3$-C$_4$-alkinylthio, C$_1$-C$_4$-alkylsulphinyl (which is optionally substituted by fluorine and/or chlorine), C$_1$-C$_4$-alkylsulphonyl (which is optionally substituted by fluorine and/or chlorine), amino, C$_1$-C$_4$-alkylamino, di-(C$_1$-C$_4$-alkyl)amino, phenyl, phenoxy, phenylthio, phenylamino, benzyl, formylamino, C$_1$-C$_4$- alkyl-carbonylamino, formyl, carbamoyl, $C_1$–$C_4$-alkyl-carbonyl and/or $C_1$–$C_4$-alkoxycarbonyl, $R^2$ represents hydrogen or $C_1$–$C_3$-alkyl, $R^3$ represents hydrogen, $C_1$–$C_4$-alkyl (which is optionally substituted by fluorine, chlorine, cyano, $C_1$–$C_4$-alkoxy or $C_1$–$C_4$-alkylthio), $C_2$–$C_4$-alkenyl (which is optionally substituted by fluorine, chlorine or phenyl), $C_2$–$C_4$-alkinyl, phenyl (which is optionally substituted by fluorine, chlorine, bromine, cyano, nitro, $C_1$–$C_4$-alkyl, trifluoromethyl, $C_1$–$C_4$-alkoxy, $C_1$–$C_2$-fluoroalkoxy, $C_1$–$C_2$-chlorofluoroalkoxy, $C_1$–$C_4$-alkylthio, $C_1$–$C_2$-fluoroalkylthio, $C_1$–$C_2$-chlorofluoroalkylthio, $C_1$–$C_4$-alkylsulphinyl, $C_1$–$C_4$-alkylsulphonyl, $C_1$–$C_2$-fluoroalkylsulphonyl, $C_1$–$C_2$-chlorofluoroalkylsulphonyl, di-($C_1$–$C_3$-alkyl)-amino or $C_1$–$C_3$-alkoxy-carbonyl), benzyl (which is optionally substituted by fluorine, chlorine, cyano, nitro, $C_1$–$C_2$-alkyl, trifluoromethyl or $C_1$–$C_3$-alkoxy-carbonyl), furyl, furylmethyl, thenyl, thienyl or pyridyl (which are optionally substituted by fluorine, chlorine or $C_1$–$C_4$-alkyl), $R^4$ represents phenyl (which is optionally substituted by fluorine, chlorine, bromine, cyano, nitro, $C_1$–$C_4$-alkyl (which is optionally substituted by fluorine and/or chlorine), $C_1$–$C_4$-alkoxy (which is optionally substituted by fluorine and/or chlorine, $C_1$–$C_4$-alkylthio (which is optionally substituted by fluorine and/or chlorine), amino, $C_1$–$C_4$-alkylamino, di-($C_1$–$C_4$-alkyl)amino or $C_1$–$C_4$-alkoxycarbonyl), naphthyl (which is optionally substituted by chlorine, cyano, nitro, amino or $C_1$–$C_4$-alkyl), pyridinyl (which is optionally substituted by fluorine, chlorine, bromine or $C_1$–$C_4$-alkyl), pyrimidinyl (which is optionally substituted by fluorine, chlorine or $C_1$–$C_4$-alkyl), imidazolyl or triazolyl and X represents oxygen, sulphur or the grouping N—$R^5$, wherein $R^5$ represents hydrogen, $C_1$–$C_4$-alkyl (which is optionally substituted by fluorine, chlorine, cyano, $C_1$–$C_4$-alkoxy, $C_1$–$C_4$-alkylthio, di-($C_1$–$C_4$-alkyl)-amino, trimethylsilyl, $C_1$–$C_4$-alkoxycarbonyl, carboxyl, carbamoyl, $C_1$–$C_4$-alkyl-aminolcarbonyl, di-($C_1$–$C_3$-alkyl)-aminocarbonyl, or by a heterocyclic grouping, as is preferably defined above for $R^1$ (inclusive of the possible substituents), $C_2$–$C_4$-alkenyl (which is optionally substituted by fluorine or chlorine), $C_2$–$C_4$-alkinyl, benzyl (which is optionally substituted by fluorine, chlorine, cyano, nitro, $C_1$–$C_2$-alkyl, trifluoromethyl, $C_1$–$C_2$-alkoxy or $C_1$–$C_2$-alkoxycarbonyl), formyl, $C_1$–$C_{20}$-alkyl-carbonyl (which is optionally substituted by fluorine, chlorine, bromine, cyano, phenyl, phenoxy or $C_1$–$C_4$-alkoxy), $C_3$–$C_6$-cycloalkyl-carbonyl (which is optionally substituted by fluorine, chlorine and/or $C_1$–$C_4$-alkyl), $C_2$–$C_{20}$-alkenyl-carbonyl (which is optionally substituted by fluorine and/or chlorine), phenylcarbonyl or naphthylcarbonyl (which are optionally substituted by fluorine, chlorine, bromine, $C_1$–$C_4$-alkyl, trifluoromethyl, cyano, nitro, $C_1$–$C_4$-alkoxy and/or $C_1$–$C_4$-alkoxycarbonyl), $C_1$–$C_{20}$-alkoxy-carbonyl, benzyloxycarbonyl, phenoxycarbonyl, $C_1$–$C_4$-alkylthiocarbonyl, benzylthio-carbonyl, phenylthio-carbonyl, $C_1$–$C_6$-alkylamino-carbonyl, di-($C_1$–$C_4$-alkyl)aminocarbonyl, phenylamino-carbonyl (which is optionally substituted by fluorine, chlorine, bromine, cyano, nitro, $C_1$–$C_4$-alkyl, trifluoromethyl, $C_1$–$C_4$-alkoxy, $C_1$–$C_2$-fluoroalkoxy, $C_1$–$C_2$-chloro-fluoroalkoxy, $C_1$–$C_4$-alkylthio, $C_1$–$C_2$-fluoroalkylthio, $C_1$–$C_2$-chlorofluoroalkylthio or $C_1$–$C_4$-alkoxycarbonyl), benzoylamino-carbonyl (which is optionally substituted by fluorine, chlorine, bromine, methyl or tri-. fluoromethyl), phenylsulphonylamino-carbonyl (which is optionally substituted by fluorine, chlorine, bromine, methyl, trifluoromethyl, $C_1$–$C_4$-alkoxy, $C_1$–$C_2$-fluoroalkoxy, $C_1$–$C_2$-chlorofluoroalkoxy or $C_1$–$C_4$-alkoxy-carbonyl), $C_1$–$C_4$-alkylthio (which is optionally substituted by fluorine and/or chlorine), phenylthio (which is optionally substituted by fluorine, chlorine, bromine, nitro or methyl), $C_1$–$C_4$-alkylsulphinyl, $C_1$–$C_4$-alkylsulphonyl (which is optionally substituted by fluorine and/or chlorine), phenylsulphinyl (which is optionally substituted by fluorine, chlorine, bromine, nitro or methyl) phenylsulphonyl or naphthylsulphonyl (which are optionally substituted by fluorine, chlorine, bromine, cyano, nitro, methyl, trifluoromethyl, $C_1$–$C_4$-alkoxy, $C_1$–$C_2$-fluoroalkoxy, $C_1$–$C_2$-chlorofluoroalkoxy and/or $C_1$–$C_4$-alkoxy-carbonyl), dimethyl(thio)phosphoryl, $C_1$–$C_4$-alkyl-$C_1$–$C_4$-alkoxy-(thio)-phosphoryl or di-($C_1$–$C_4$-alkoxy)-(thio)phosphoryl.

The invention relates in particular to compounds of the formula (I) in which m represents the numbers 0, 1 or 2, A represents ethane-1,2-diyl (dimethylene) or propane-1,3-diyl (trimethylene), $R^1$ represents a five- or six-membered heterocyclic grouping from the series comprising pyrazolyl, 1,2,4-triazolyl, oxazolyl, isoxazolyl, thiazolyl, isothiazolyl, 1,2,5-thiadiazolyl, pyridyl, pyrazinyl and pyrimidinyl, each of which is optionally substituted by fluorine, chlorine, bromine, cyano, nitro, $C_1$–$C_2$-alkyl (which is optionally substituted by fluorine and/or chlorine), $C_1$–$C_2$-alkoxy (which is optionally substituted by fluorine and/or or chlorine), $C_1$–$C_2$-alkylthio (which is optionally substituted by fluorine and/or chlorine) or $C_1$–$C_2$-alkylsulphonyl (which is optionally substituted by fluorine and/or chlorine), $R^2$ represents hydrogen, $R^3$ represents hydrogen, $R^4$ represents phenyl (which is optionally substituted by fluorine, chlorine, $C_1$–$C_4$-alkyl, trifluoromethyl, $C_1$–$C_2$-alkoxy (which is optionally substituted by fluorine and/or chlorine) or $C_1$–$C_2$-alkoxy-carbonyl) or naphthyl and X represents sulphur or the grouping N—$R^5$, wherein $R^5$ represents hydrogen, methyl, ethyl, allyl, propargyl, formyl, $C_1$–$C_8$-alkyl-carbonyl, phenylcarbonyl (which is optionally substituted by fluorine and/or chlorine), $C_1$–$C_8$-alkoxy-carbonyl, benzyloxycarbonyl, phenoxy-carbonyl, benzyl (which is optionally substituted by fluorine or chlorine) or di-($C_1$–$C_2$-alkoxy)-(thio)phosphoryl. If, for example, 1-(2-chlorothiazol-5-yl-methyl)-2-nitroiminoimidazolidine, acetaldehyde and thiophenol are used as starting materials when carrying out the preparation process according to the invention for the compounds of the general formula (I), then the reaction of these compounds can be outlined by the following equation:

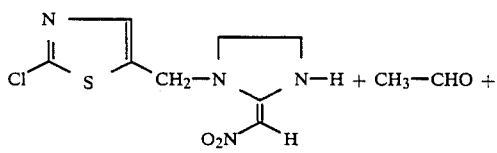

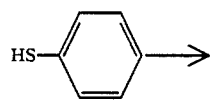

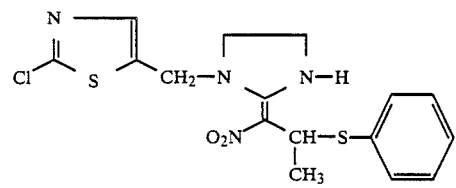

Formula (II) provides a general definition of the nitroalkenes to be used as starting materials in the preparation process according to the invention. In this formula (II), A, $R^1$, $R^2$ and X preferably or particularly have the same meanings as have already preferably or particularly preferably been mentioned in connection with the description of the compounds of the formula (I) according to the invention.

Examples of the starting materials of the formula (II) are shown in Table 1 below.

TABLE 1

| A | $R^1$ | $R^2$ | X |
|---|---|---|---|
| CH₂CH₂ | 3-pyridyl | H | NH |
| CH₂CH₂ | 6-chloro-3-pyridyl | H | NH |
| CH₂CH₂ | 2-chloro-thiazol-5-yl | H | NH |
| CH₂CH₂ | 3-pyridyl | H | S |
| CH₂CH₂ | 6-chloro-3-pyridyl | H | S |
| CH₂CH₂ | 2-chloro-thiazol-5-yl | H | S |
| (CH₂)₃ | 6-chloro-3-pyridyl | H | S |
| (CH₂)₃ | 3-pyridyl | H | S |
| (CH₂)₃ | 1-methyl-pyrazol-3-yl | H | NH |

TABLE 1-continued

Examples of starting materials of the formula (II)

| A | R¹ | R² | X |
|---|---|---|---|
| CH₂CH₂ | 3-methyl-5-methylisoxazol-4-yl (N—O ring, H₃C, CH₃) | H | NH |
| CH₂CH₂ | 5-methylisoxazol-3-yl (N—O ring) | H | NH |
| (CH₂)₃ | 2-methyl-4-methylthiazol-5-yl (H₃C, S) | H | NH |
| CHPHD 2CH₂ | 6-fluoropyridin-3-yl (F, N) | H | NH |
| (CH₂)₃ | 6-chloropyridin-3-yl (Cl, N) | H | NH |
| CH₂CH₂ | 6-(2,2,2-trifluoroethoxy)pyridin-3-yl (F₃CCH₂O, N) | H | NH |
| CH₂CH₂ | pyrimidin-5-yl (N, N) | H | NH |
| CH₂CH₂ | 5-methylpyrazin-2-yl (H₃C, N, N) | H | NH |
| CH₂CH₂ | 6-chloropyridin-3-yl (Cl, N) | H | O |
| CH₂CH₂ | 1,2,5-thiadiazol-3-yl (N, S, N) | H | NH |
| CH₂CH₂ | 2-chloro-4-methylthiazol-5-yl (N, Cl, S) | H | NCH₃ |
| CH₂CH₂ | pyridin-4-yl (N) | H | S |
| CH₂CH₂ | 6-chloropyridin-3-yl (Cl, N) | H | N—CO—C₄H₉ |

TABLE 1-continued

Examples of starting materials of the formula (II)

| A | R¹ | R² | X |
|---|---|---|---|
| CH₂CH₂ | 2-chloro-4-methylthiazol-5-yl | H | N—CHO |
| CH₂CH₂ | 3-methyl-5-isoxazolyl | H | S |
| CH₂CH₂ | 6-chloropyridin-3-yl | H | N—CO—CH₃ |
| CH₂CH₂ | 3-methyl-5-isoxazolyl | H | N—COOCH₃ |
| CH₂CH₂ | 6-(trifluoromethyl)pyridin-3-yl | H | NH |
| (CH₂)₃ | 6-fluoropyridin-3-yl | H | S |
| CH₂CH₂ | 6-bromopyridin-3-yl | H | NH |
| CH₂CH₂ | 6-chloropyridin-3-yl | H | N—CO—C₆H₅ |
| CH₂CH₂ | 2-chloro-4-methylthiazol-5-yl | H | N—COOC₄H₉ |
| CH₂CH₂ | 2-chloro-4-methylthiazol-5-yl | H | NCH₂CH=CH₂ |
| CH₂CH₂ | 6-chloropyridazin-3-yl | H | N—COO—C₆H₅ |
| CH₂CH₂ | 6-chloropyridin-3-yl | H | N—P(O)(OCH₃)₂ |
| (CH₂)₃ | 6-chloropyridazin-3-yl | H | N—CO—NH—C₆H₅ |

TABLE 1-continued

Examples of starting materials of the formula (II)

| A | R¹ | R² | X |
|---|---|---|---|
| CH₂CH₂ | (4-chloropyridin-2-yl) | H | N—CH₂—(phenyl) |
| (CH₂)₃ | (4-chloro-5-methylthiazol-2-yl) | H | N—CH₂C≡CH |
| CH₂CH₂ | (4-chloro-5-methylthiazol-2-yl) | H | N—CO—NH—CO—(2-fluorophenyl) |
| CH₂CH₂ | (4-chloropyridin-2-yl) | H | N—CO—NH—SO₂—(4-methylphenyl) |
| CH₂CH₂ | (4-methylpyridin-2-yl) | H | NH |

The starting materials of the formula (II) are known and/or can be prepared by processes known per se (compare EP-A No. 192,060).

Formula (III) provides a general definition of the aldehydes to be further used as starting materials. In this formula (III), $R^3$ preferably or particularly has the same meaning as has already preferably or particularly preferably been given in connection with the description of the compounds of the formula (I) according to the invention.

Examples of the starting materials of the formula (III) which may be mentioned are: formaldehyde, acetaldehyde, propionaldehyde, butyraldehyde, chloroacetaldehyde, dichloroacetaldehyde, trichloroacetaldehyde, crotonaldehyde, cinnamaldehyde, benzaldehyde, phenylacetaldehyde, furfural and pyridine-2-, -3- and -4-carboxaldehyde.

The starting materials of the formula (III) are known chemicals.

Formula (IV) provides a general definition of the mercapto compounds further to be used as starting materials. In this formula (IV), $R^4$ preferably or particularly has the same meaning as has already preferably or particularly preferably been given in connection with the description of the compounds of the formula (I) according to the invention.

Examples of the starting materials of the formula (IV) which may be mentioned are:
thiophenol, 2-chloro-, 3-chloro- and 4-chloro-thiophenol, 2-fluoro-, 3-fluoro- and 4-fluoro-thiophenol, 2-bromo-, 3-bromo- and 4-bromo-thiophenol, 2,3-dichloro-, 2,4-dichloro-, 2,5-dichloro-, 2,6-dichloro-, 3,4-dichloro- and 3,5-dichloro-thiophenol, 4-methyl-, 4-ethyl-, 4-propyl-, 4-isopropyl-, 4-butyl-, 4-isobutyl-, 4-sec-butyl- and 4-tert-butyl-thiophenol, 3-methoxy- and 4-methoxy-thiophenol, 2-methoxycarbonyl-, 2-ethoxycarbonyl-, 4-methoxycarbonyl- and 4-ethoxycarbonyl-thiophenol and also naphthalene-1-thiol and naphthalene-2-thiol.

The starting materials of the formula (IV) are known chemicals.

The process according to the invention for the preparation of the new substituted nitroalkenes of the formula (I) is preferably carried out using diluents. Suitable diluents are, in particular, protic polar solvents, such as water, alcohols (such as, for example, methanol, ethanol, propanol, isopropanol, butanol, isobutanol and tertbutanol) and alkanediols or derivatives (such as, for example, ethane-1,2-diol and 2-methoxyethanol) and also mixtures of these solvents, but also less polar solvents (such as, for example, benzene, toluene, dioxane and nitrobenzene).

The process according to the invention is carried out, where appropriate, in the presence of acids. Suitable acids are preferably protic acids such as, for example, hydrochloric acid, sulphuric acid, phosphoric acid, acetic acid, methanesulphonic acid, benzenesulphonic acid, p-toluenesulphonic acid and naphthalene-1- or -2-sulphonic acid.

The reaction temperatures can be varied within a relatively wide range in the process according to the invention. In general, the reaction is carried out at temperatures between 0° C. and 120° C., preferably at temperatures between 10° C. and 100° C.

The process according to the invention is generally carried out at atmospheric pressure or slightly elevated pressure.

For carrying out the process according to the invention, 1.0 to 1.2 moles, preferably 1.0 to 1.05 moles, of aldehyde of the formula (III) and 1.0 to 1.5 moles, preferably 1.0 to 1.2 moles, of mercapto compound of the formula (IV) are generally employed per mole of starting compound of the formula (II).

In general, the starting material of the formula (II) is mixed at room temperature with the solvent and then successively with the mercapto compound of the formula (IV) and the aldehyde of the formula (III) and the reaction mixture is then stirred and/or heated under reflux to boiling until completion of the reaction, if appropriate at elevated temperature.

The products of the formula (I) are generally precipitated as crystals on cooling and can be isolated by filtering off with suction.

The compounds of the formula (I) thus obtained—m=0—can be converted into corresponding sulphoxides—m=1—or sulphones—m=2—by customary oxidation methods (compare Tetrahedron 42 (1986), 5459–5495), for example by reaction with hydrogen peroxide in the presence of selenium dioxide in methanol/water (compare Synthesis 1978, 758–759), in the presence of titanium(III) chloride in methylene chloride/water (compare Synthesis 1981, 204–205), in the presence of sodium tungstate in water (compare EP-A No. 137,417) or by reaction with alkali metal hypochlorites in water (compare EP-A No. 125,654) at temperatures between 0° C. and 50° C.

The active compounds are suitable for combating animal pests, preferably arthropods and nematodes, in particular insects and arachnida encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera spec.* From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americans, Leucophaea maderae, Blattella germanica, Acheta domesticus,* Gryllotalpa spp., Locusta migratoria migratoriodides, *Melanoplus differentialis* and *Schistocerca gregaris.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp., and Linognathus spp. From the order of the Mallophaga, for example, Trichodectes spp. and Damalinea spp. From the order of the Thysanoptera, for example, *Hercinothrips femoralis* and *Thrips tabaxi.* From the order of the Heteroptera, for example, Eurygaster spp., *Dysdercus intermedium, Piesma quadrate, Cimex lectularius, Rhondnius prolixus* and Triatoma spp. From the order of the Homoptera, for example, *Aleurodes brassicate, Bemisia tabaci, Trialeurodes vaporariorum, Aphis gossypii, Brevicoryne brassicae, Cryptomyzua ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Cuscelis bilobatus, Nephotettix cincticeps, Lecanium corni, Saissetia oleae, Laodelphax striatellus, Nilaparvata lugens, Aonidiella aurantii, Aspidiotus hederae,* Pseudococus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euprocic cyrysorrhoes,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthreneus spp., Attagenus spp., Lyctus spp., *Meligethers aeneus,* Ptinus spp., *Niptus holoeucus, Gibbium psylloides,* Tribolium spp., *Tenebrio molitor,* Agriotes spp., Conoderus spp., *Melolontha melolontha, Amphimallon solstrtialis* and *Costelytra zealandica.* From the order of the Hymenoptera, for example, Diprion spp., Hoplocampa spp., Lasium spp., *Monomorium pharaonis* and Vespa spp. From the order of the Diptera, for example, Aedes spp., Anopheles spp., Fannia spp., *Calliphor erythrocephala,* Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit,* Phorbia spp., *Pegomyis hyoscyami,Ceratities capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., and Tetranychus spp.

The phytoparasitic nematode include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp.

The active compounds of the formula (I) according to the invention are distinguished by outstanding insecticidal activity. In particular, they show outstanding action when employed as leaf insecticides and soil insecticides, for example against beetle larvae (for example *Phaedon cochleariae*), against caterpillars (for example *Spodoptera frugiperda*) and against aphids (for example *Myzus persicae*).

The active compounds of the formula according to the invention are also suitable for combating arthropods which infest agricultural productive livestock such as, for example, cattle, sheep, goats, horses, pigs, donkeys, camels, buffalo, rabbits, chickens, turkeys, ducks, geese and bees, pets, such as, for example, dogs, cats, cage birds and aquarium fish, and also so-called experimental animals, such as, for example, hamsters, guinea pigs, rats and mice.

By combating these arthropods, it is intended that cases of death and reductions in productivity (for meat, milk, wool, hides, eggs, honey etc.) be diminished, so that more economic and straightforward animal husbandry is possible by use of the active compounds according to the invention.

The active compounds according to the invention are used in the veterinary sector in a known manner by enteral administration in the form of, for example, tablets, capsules, potions, drenches, granules, pastes, boli, the feed-through process and suppositories, by parenteral administration, such as, for example, by injections (intramuscular, subcutaneous, intravenous, intraperitioneal etc), implants, by nasal administration, by dermal use in the form, for example, of dipping or bathing, spraying, pouring on and spotting on, washing and powdering, and also with the aid of molded articles containing the active compound, such as collars, ear tags, tail tags, limb bands, halters, marking devices, etc.

Depending on their respective physical and/or chemical properties, the active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and furthermore into formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolyzation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

PREPARATION EXAMPLES

EXAMPLE 1

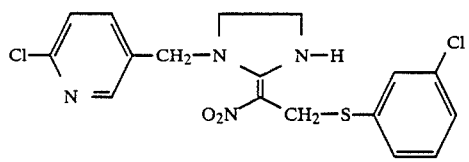

10 ml of a 35% strength aqueous formaldehyde solution (corresponding to 0.12 mol) are added dropwise at 25° C. with stirring to a mixture of 25.4 g (0.10 mol) of 1-(2-chloro-pyridin-5-yl-methyl)-2-nitromethylene-imidazolidine, 14.4 g (0.10 mol) of 3-chloro-thiophenol and 500 ml of ethanol and the reaction mixture is then heated to boiling under reflux for five hours. After cooling to 20° C., the precipitated crystalline product is isolated by filtering off with suction.

31 g (69% of theory) of 1-(2-chloro-pyridin-5-yl-methyl)-2-(1-nitro-2-(3-chloro-phenylthio)-ethylidene)imidazolidine of melting point 143° C. are obtained.

The compounds of the general formula (I) shown in Table 2 below can be prepared analogously to Example 1 and corresponding to the general description of the preparation process according to the invention.

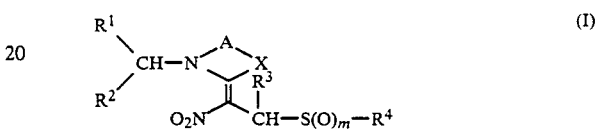

TABLE 2

Examples of compounds of the formula (I)

| Example No. | m | A | R¹ | R² | R³ | R⁴ | X | Melting point (°C.) |
|---|---|---|---|---|---|---|---|---|
| 2 | 0 | CH₂CH₂ | 2-Cl-pyridin-5-yl | H | H | phenyl | NH | 164 |
| 3 | 0 | CH₂CH₂ | 2-Cl-pyridin-5-yl | H | H | 2-Cl-phenyl | NH | 157 |
| 4 | 0 | CH₂CH₂ | 2-Cl-pyridin-5-yl | H | H | 4-CH₃-phenyl | NH | 157 |
| 5 | 0 | CH₂CH₂ | 2-Cl-pyridin-5-yl | H | H | 4-Cl-phenyl | NH | 156 |
| 6 | 1 | CH₂CH₂ | 2-Cl-pyridin-5-yl | H | H | phenyl | NH | — |
| 7 | 0 | CH₂CH₂ | 2-Cl-thiazol-5-yl | H | H | 4-F-phenyl | NH | 126 |
| 8 | 0 | CH₂CH₂ | 2-Cl-thiazol-5-yl | H | H | phenyl | NH | 146 |

TABLE 2-continued
Examples of compounds of the formula (I)
| Example No. | m | A | R¹ | R² | R³ | R⁴ | X | Melting point (°C.) |
|---|---|---|---|---|---|---|---|---|
| 9 | 0 | (CH₂)₃ | 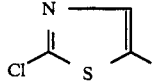 | H | H | 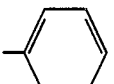 | S | |
| 10 | 0 | CH₂CH₂ | 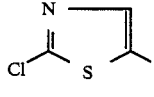 | H | H | 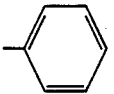 | S | |
| 11 | 0 | CH₂CH₂ | 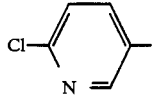 | H | H | 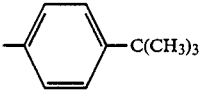—C(CH₃)₃ | NH | 200 |
| 12 | 0 | CH₂CH₂ | 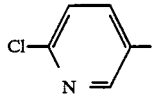 | H | H | 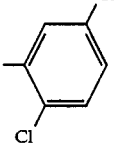 | NH | 167 |
| 13 | 1 | (CH₂)₃ | 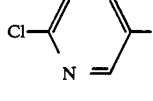 | H | H | 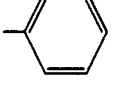 | NH | |
| 14 | 2 | (CH₂)₃ | 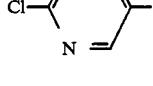 | H | H | 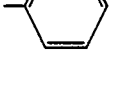 | NH | |
| 15 | 0 | CH₂CH₂ | 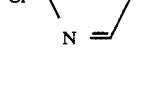 | H | H | 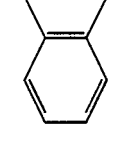 | NH | 162 |
| 16 | 0 | CH₂CH₂ | 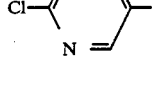 | H | CH₃ | 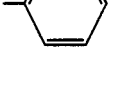 | NH | |
| 17 | 0 | CH₂CH₂ | 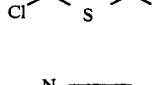 | H | CH₃ | 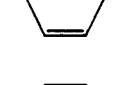—F | NH | |
| 18 | 0 | CH₂CH₂ |  | H | CCl₃ | 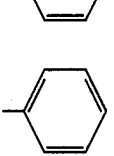 | NH | |
| 19 | 1 | CH₂CH₂ | 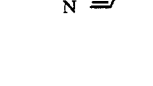 | H | CCl₃ |  | NH | |

TABLE 2-continued
Examples of compounds of the formula (I)
| Example No. | m | A | R¹ | R² | R³ | R⁴ | X | Melting point (°C.) |
|---|---|---|---|---|---|---|---|---|
| 20 | 0 | CH₂CH₂ | 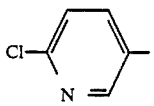 | H | H | 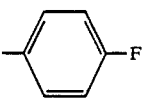 | NH | 153 |
| 21 | 0 | CH₂CH₂ | 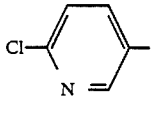 | H | H | 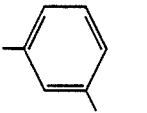 | NH | 134 |
| 22 | 0 | CH₂CH₂ | 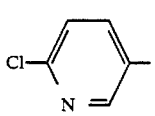 | H | H | 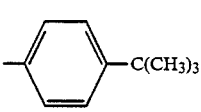 | NH | |
| 23 | 1 | CH₂CH₂ | 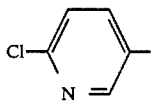 | H | H | 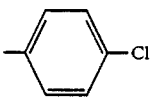 | NH | |
| 24 | 2 | CH₂CH₂ | 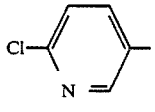 | H | H | 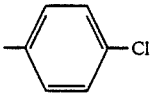 | NH | |
| 25 | 0 | (CH₂)₃ | 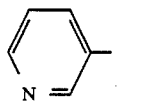 | CH₃ | H | 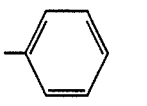 | S | |
| 26 | 0 | CH₂CH₂ | 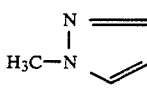 | H | H | 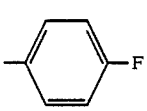 | NH | |
| 27 | 0 | CH₂CH₂ | 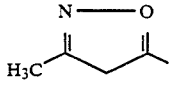 | H | H | 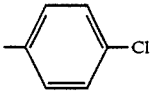 | NH | |
| 28 | 1 | (CH₂)₃ | 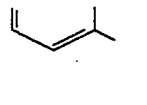 | H | H | 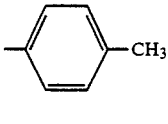 | S | |
| 29 | 0 | CH₂CH₂ | 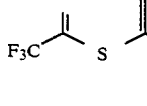 | H | H | 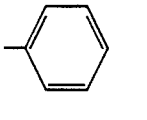 | NH | |
| 30 | 2 | (CH₂)₃ | 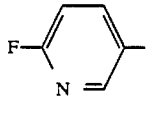 | H | H | 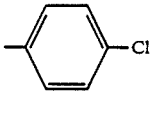 | S | |
| 31 | 0 | CH₂CH₂ | 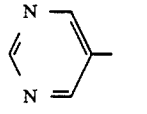 | H | H | 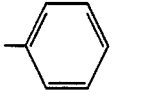 | NH | |

TABLE 2-continued
Examples of compounds of the formula (I)
| Example No. | m | A | R¹ | R² | R³ | R⁴ | X | Melting point (°C.) |
|---|---|---|---|---|---|---|---|---|
| 32 | 0 | CH₂CH₂ | 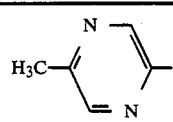 | H | H | 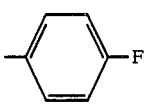 | NH | |
| 33 | 0 | CH₂CH₂ | 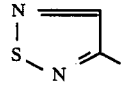 | H | H | 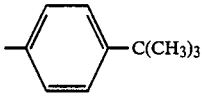 | NH | |
| 34 | 0 | CH₂CH₂ | 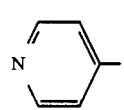 | H | H |  | NH | |
| 35 | 0 | CH₂CH₂ | 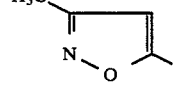 | H | H | 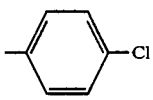 | NH | |
| 36 | 0 | CH₂CH₂ | 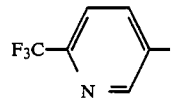 | H | H | 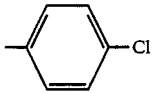 | NH | |
| 37 | 0 | CH₂CH₂ | 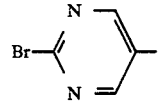 | H | H |  | NH | |
| 38 | 0 | CH₂CH₂ | 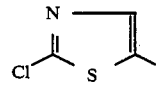 | H | H |  | NCH₃ | |
| 39 | 0 | CH₂CH₂ | 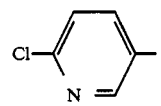 | H | H | 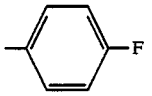 | N—CO—C₄H₉ | |
| 40 | 0 | CH₂CH₂ | 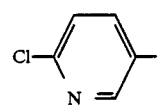 | H | H | 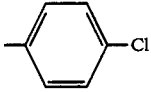 | N—COOCH₃ | |
| 41 | 0 | (CH₂)₃ | 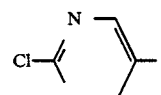 | H | H |  | NCH₂CH=CH₂ | |
| 42 | 0 | CH₂CH₂ | 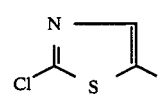 | H | H | 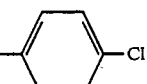 | N—P(S)(OC₂H₅)₂ | |
| 43 | 0 | CH₂CH₂ | 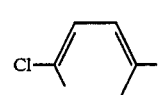 | H | H |  | N—CO—NHCH₃ | |
| 44 | 0 | CH₂CH₂ | 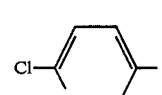 | H | H |  | N—CO— | |

TABLE 2-continued

| | | | Examples of compounds of the formula (I) | | | | |
|---|---|---|---|---|---|---|---|
| Example No. | m | A | R¹ | R² | R³ | R⁴ | X | Melting point (°C.) |
| 45 | 0 | CH₂CH₂ | 5-Cl-pyridin-2-yl | H | H | phenyl | S | |
| 46 | 0 | (CH₂)₃ | 5-Cl-pyridin-2-yl | H | H | phenyl | S | |
| 47 | 0 | CH₂CH₂ | 5-CH₃-pyridin-2-yl | H | H | 4-F-phenyl | NH | |
| 48 | 0 | CH₂CH₂ | 5-Cl-pyridin-2-yl | H | H | 4-Cl-phenyl | S | |

USE EXAMPLES

The compound given below is employed as comparison substance in the following use examples:

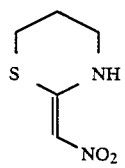
(A)

2-nitromethylene-2H-tetrahydro-1,3-thiazine (compare U.S. Pat. No. 3,993,648).

EXAMPLE A

Phaedon larvae test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of the active compound of the desired concentration and are infested with mustard beetle larvae (Phaedon cochleariae), as long as the leaves are still moist.

After the desired period of time, the destruction in % is determined. 100% means that all the beetle larvae have been killed; 0% means that none of the beetle larvae have been killed.

In this test, the compounds obtained according to the preparation examples (1), (2), (3), (4), (5), (8), (11), (12), (15), (20) and (21) show an action of between 50% and 100% after 3 days at an active compound concentration of 0.001%, whereas the comparison substance (A) shows no detectable action.

EXAMPLE B

Spodoptera test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of active compound of the desired concentration and are infested with caterpillars of the owlet moth (Spodoptera frugiperda), as long as the leaves are still moist.

After the desired period of time, the destruction in % is determined. 100% means that all the caterpillars have been killed; 0% means that none of the caterpillars have been killed.

In this test, the compounds obtained according to the preparation examples (1), (2), (4) and (11) show an action between 90% and 100% after 3 days at an active compound concentration of 0.001%, whereas the comparison substance (A) shows no detectable action.

EXAMPLE C

Myzus test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which have been heavily infested with the peach aphid (*Myzus persicae*) are treated by being dipped into the preparation of active compound of the desired concentration.

After the desired period of time, the destruction in % is determined. 100% means that all the aphids have been killed; 0% means that none of the aphids have been killed.

In this test, the compounds obtained according to the preparation examples (1), (3), (4), (5), (7), (15), (20) and (21) show an action between 80% and 100% after one day at an active compound concentration of 0.001%, whereas the comparison substance (A) only shows an action of 10%.

EXAMPLE D

Critical concentration test/root-systemic action
Test insect: Phaedon cochleariae
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test animals after 7 days. After a further 2 days, the evaluation is made by counting or estimating the dead animals. The root-systemic action of the active compound is deduced from the mortality figures. It is 100% if all test animals have been killed and 0% if just as many test insects are still alive as in the case of the untreated control.

In this test, the compounds obtained according to the preparation examples (1), (2), (3), (4) and (5) show an action of 100% at an active compound concentration of 20 ppm, whereas the comparison substance (A) shows no detectable action.

EXAMPLE E

Critical concentration test/root-systemic action
Test insect: *Myzus persicae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test animals after 7 days. After a further 2 days, the evaluation is made by counting or estimating the dead animals. The root-systemic action of the active compound is deduced from the mortality figures. It is 100% if all test animals have been killed and 0% if just as many test insects are still alive as in the case of the untreated control.

In this test, the compounds obtained according to the preparation examples (1), (2), (3), (4) and (5) show an action of 100% at an active compound concentration of 20 ppm, whereas the comparison substance (A) shows no detectable action.

EXAMPLE F

Test with *Lucilia cuprina* resistant larvae
Emulsifier:
35 parts by weight of ethylene glycol monomethyl ether
35 parts by weight of nonyl phenol polyglycol ether To produce a suitable preparation of active compound, three parts by weight of active compound are mixed with seven parts by weight of the abovementioned mixture and the concentrate thus obtained is diluted with water to the particular desired concentration.

About 20 *Lucilia cuprina* res. larvae are introduced into a test tube which contains approx. 1 cm³ of horse flesh and 0.5 ml of the preparation of active compound. After 24 hours, the degree of destruction is determined.

In this test, for example, the following compounds from the preparation examples show a superior action compared to the prior art: (1), (2), (3), (4), (5), (7), (8) and (11).

What is claimed is:

1. A substituted nitroalkene of the formula

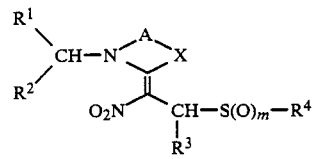

in which
m represents the numbers 0, 1 or 2
A represents a $C_2$-alkanediyl,
$R_1$ represents pyridyl which is unsubstituted or substituted by halogen, cyano, nitro, alkyl, halogenoalkyl, alkenyl, halogenoalkenyl, alkinyl, alkoxy, halogenoalkoxy, alkenyloxy, halogenoalkenyloxy, alkinyloxy, alkylthio, halogenoalkylthio, alkenylthio, halogenoalkenylthio, alkinylthio, alkylsulphinyl, halogenoalkylsulphinyl, alkylsulphonyl, halogenoalkylsulphonyl, amino, alkylamino, dialkylamino, aryl, aryloxy, arylthio, arylamino, aralkyl, formylamino, alkylcarbonylamino, formyl, carbamoyl, alkylcarbonyl or alkoxycarbonyl, $R^2$ represents hydrogen or alkyl, $R^3$ represents hydrogen; alkyl which is unsubstituted or substituted by halogen, cyano, alkoxy or alkylthio; alkenyl which is unsubstituted or substituted by halogen or phenyl; alkinyl; phenyl which is unsubstituted or substituted by halogen, cyano, nitro, alkyl, halogenoalkyl, alkoxy, halogenoalkoxy, alkylthio, halogenoalkylthio, alkylsulphinyl, alkylsulphonyl, halogenoalkylsulphonyl, dialkylamino or alkoxycarbonyl; benzyl which is unsubstituted or substituted by halogen, cyano, nitro, alkyl, halogenoalkyl or alkoxycarbonyl; furyl, furylmethyl, thenyl, thienyl or pyridyl which are unsubstituted or substituted by halogen or alkyl;

$R^4$ represents phenyl which is unsubstituted or substituted by halogen, cyano, nitro, alkyl, halogenoalkyl, alkoxy, halogenoalkoxy, alkylthio, halogenoalkylthio, amino, alkylamino, dialkylamino, or alkoxycarbonyl; naphthyl which is unsubstituted or substituted by halogen, cyano, nitro, alkyl or amino; pyridinyl which is unsubstituted or substituted by halogen or alkyl; imidazolyl or triazolyl and X represents oxygen, sulphur or the grouping N—$R^5$, wherein $R^5$ represents hydrogen; alkyl which is unsubstituted or substituted by halogen, cyano, alkoxy, alkylthio, dialkylamino, trialkylsilyl, alkoxycarbonyl, carbonyl, carbamoyl, alkylaminocarbonyl, dialkylaminocarbonyl or by the radical $R^1$; alkenyl which is unsubstituted or substituted by halogen; alkinyl; benzyl which is unsubstituted or substituted by halogen, cyano, nitro, alkyl, halogenoalkyl, alkoxy or alkoxycarbonyl; formyl; alkylcarbonyl which is unsubstituted or substituted by halogen, cyano, phenyl, phenoxy or alkoxy; cycloalkylcarbonyl which is unsubstituted or substituted by halogen or alkyl; alkenylcarbonyl which is unsubstituted or substituted by halogen; phenylcarbonyl or naphthylcarbonyl which are unsubstituted or substituted by halogen, alkyl, halogenoalkyl, cyano, nitro, alkoxy or alkoxycarbonyl; alkoxycarbonyl; benzyloxycarbonyl; phenoxycarbonyl; alkylthiocarbonyl; benzylthiocarbonyl; phenylthiocarbonyl; alkylaminocarbonyl; dialkylaminocarbonyl; phenylaminocarbonyl which is unsubstituted or substituted by halogen, cyano, nitro, alkyl, halogenoalkyl, alkoxy, halogenoalkoxy, alkylthio, halogenoalkylthio or alkoxycarbonyl; benzoylaminocarbonyl which is unsubstituted or substituted by halogen, alkyl, halogenoalkyl, alkoxy, halogenoalkoxy or alkoxycarbonyl; alkylthio which is unsubstituted or substituted by halogen; phenylthio which is unsubstituted by halogen, nitro or alkyl; phenylsulphonyl or naphthylsulphonyl which are unsubstituted or substituted by halogen, cyano, nitro, alkyl, halogenoalkyl, alkoxy, halogenoalkoxy or alkoxycarbonyl; dialkyl(thio)phosphoryl; alkylalkoxy-(thio)phosphoryl or dialkoxy(thio)phosphoryl.

2. A substituted nitroalkene according to claim 1 in which m represents the numbers 0, 1 or 2, A represents $C_2$-alkanediyl, $R_1$ represents pyridyl which is unsubstituted or substituted by fluorine, chlorine, bromine, iodine, cyano or nitro; $C_2$–$C_4$-alkyl which is unsubstituted or substituted by fluorine or chlorine; $C_2$–$C_4$-alkenyl which is unsubstituted or substituted by fluorine or chlorine; $C_2$–$C_4$-alkinyl; $C_1$–$C_4$-alkoxy which is unsubstituted or substituted by fluorine or chlorine; $C_3$–$C_4$-alkenyloxy which is unsubstituted or substituted by fluorine or chlorine; $C_3$–$C_4$-alkinyloxy; $C_1$–$C_4$-alkylthio which is unsubstituted or substituted by fluorine or chlorine; $C_3$–$C_4$-alkenylthio which is unsubstituted or substituted by fluorine or chlorine; $C_3$–$C_4$-alkinylthio; $C_1$–$C_4$-alkylsulphinyl which is unsubstituted or substituted by fluorine or chlorine; $C_1$–$C_4$-alkylsulphonyl which is unsubstituted or substituted by fluorine or chlorine; amino; $C_1$–$C_4$-alkyl-amino; di-($C_1$–$C_4$-alkyl)amino; phenyl; phenoxy; phenylthio; phenylamino; benzyl; formylamino; $C_1$–$C_4$-alkylcarbonylamino; formyl; carbamoyl; $C_1$–$C_4$-alkylcarbonyl or $C_1$–$C_4$-alkoxy-carbonyl, $R^2$ represents hydrogen or $C_1$–$C_3$-alkyl, $R^3$ represents hydrogen; $C_1$–$C_4$-alkyl which is unsubstituted or substituted by fluorine, chlorine, cyano, $C_1$–$C_4$-alkoxy or $C_1$–$C_4$-alkylthio; $C_2$–$C_4$-alkenyl which is unsubstituted or substituted by fluorine, chlorine or phenyl; $C_2$–$C_4$-alkinyl; phenyl which is unsubstituted or substituted by fluorine, chlorine, bromine, cyano, nitro, $C_1$–$C_4$-alkyl, trifluoromethyl, $C_1$–$C_4$-alkoxy, $C_1$–$C_2$-fluoroalkoxy, $C_1$–$C_2$-chlorofluoroalkoxy, $C_1$–$C_4$-alkylthio, $C_1$–$C_2$-fluoroalkylthio, $C_1$–$C_2$-chlorofluoroalkylthio, $C_1$–$C_4$-alkylsulphinyl, $C_1$–$C_4$-alkylsulphonyl, $C_1$–$C_2$-fluoroalkylsulphonyl, $C_1$–$C_2$-chlorofluoroalkylsulphonyl, di-($C_1$–$C_3$-alkyl)-amino or $C_1$–$C_3$-alkoxy-carbonyl; benzyl which is unsubstituted or substituted by fluorine, chlorine cyano, nitro, $C_1$–$C_3$-alkoxy-carbonyl; furyl, furylmethyl, thenyl, thienyl or pyridyl which are unsubstituted or substituted by fluorine, chlorine or $C_1$–$C_4$-alkyl, $R^4$ represents phenyl which is unsubstituted or substituted by fluorine, chlorine, bromine, cyano, nitro; $C_1$–$C_4$-alkyl which is unsubstituted or substituted by fluorine or chlorine; $C_1$–$C_4$-alkoxy which is unsubstituted or substituted by fluorine or chlorine; $C_1$–$C_4$-alkylthio which is unsubstituted or substituted by fluorine or chlorine; amino; $C_1$–$C_4$-alkylamino; di($C_1$–$C_4$-alkyl)-amino or $C_1$–$C_4$-alkoxycarbonyl; naphthyl which is unsubstituted or substituted by chlorine, cyano, nitro, amino or $C_1$–$C_4$-alkyl; pyridinyl which is unsubstituted or substituted by fluorine, chlorine, bromine or $C_1$–$C_4$-alkyl; imidazolyl or triazolyl and X represents oxygen, sulphur or the grouping N—$R^5$, wherein $R^5$ represents hydrogen; $C_1$–$C_4$-alkyl which is unsubstituted or substituted by fluorine, chlorine, cyano, $C_1$–$C_4$-alkoxy, $C_1$–$C_4$-alkylthio, di-($C_1$–$C_4$-alkyl)-amino, trimethylsilyl, $C_1$–$C_4$-alkoxy-carbonyl, carboxyl, carbamoyl, $C_1$–$C_4$-alkyl-amino-carbonyl, di-($C_1$–$C_3$-alkyl)-aminocarbonyl, or by the radical $R_1$; $C_2$–$C_4$-alkenyl which is unsubstituted or substituted by fluorine or chlorine; $C_2$–$C_4$-alkinyl; benzyl which is unsubstituted or substituted by fluorine, chlorine, cyano, nitro, $C_1$–$C_2$-alkyl, trifluoromethyl, $C_1$–$C_2$-alkoxy or $C_1$–$C_2$-alkoxy-carbonyl; formyl; $C_1$–$C_{20}$-alkyl-carbonyl which is unsubstituted or substituted by fluorine, chlorine, bromine, cyano, phenyl, phenoxy or $C_1-C_4$-alkoxy; $C_3-C_6$-cycloalkyl-carbonyl which is unsubstituted or substituted by fluorine, chlorine or $C_1-C_4$-alkyl; $C_2-C_{20}$-alkenyl-carbonyl which is unsubstituted or substituted by fluorine or chlorine; phenylcarbonyl or naphthylcarbonyl which are unsubstituted or substituted by fluorine, chlorine, bromine, $C_1-C_4$-alkyl, trifluoromethyl, cyano, nitro, $C_1-C_4$-alkoxy or $C_1-C_4$-alkoxy-carbonyl; $C_1-C_{20}$-alkoxy-carbonyl; benzyloxy carbonyl; phenoxycarbonyl; $C_1-C_4$-alkylthio-carbonyl; benzylthio-carbonyl; phenylthio-carbonyl; $C_1-C_4$-alkylamino-carbonyl; di-($C_1-C_4$-alkyl)-amino-carbonyl; phenylamino-carbonyl which is unsubstituted or substituted by fluorine, chlorine, bromine, cyano, nitro, $C_1-C_4$-alkyl, trifluoromethyl, $C_1-C_4$-alkoxy, $C_1-C_2$-fluoroalkoxy, $C_1-C_2$-chlorofluoroalkoxy, $C_1-C_4$-alkylthio, $C_1-C_2$-fluoroalkylthio, $C_1-C_2$-chlorofluoro-alkylthio or $C_1-C_4$-alkoxy-carbonyl; benzoyl-amino-carbonyl which is unsubstituted or substituted by fluorine, chlorine, bromine, methyl or trifluoromethyl; phenylsulphonylamino-carbonyl which is unsubstituted or substituted by fluorine, chlorine, bromine, methyl, trifluoromethyl, $C_1-C_4$-alkoxy or $C_1-C_4$-fluoroalkoxy, $C_1-C_2$-chlorofluoro-alkoxy or $C_1-C_4$-alkoxy-carbonyl; $C_1-C_4$-alkyl-thio which is unsubstituted or substituted by fluorine or chlorine; phenylthio which is unsubstituted or substituted by fluorine, chlorine, bromine, nitro or methyl; $C_1-C_4$-alkylsulphinyl; $C_1-C_4$-alkyl-sulphonyl which is unsubstituted or substituted by fluorine or chlorine; phenylsulphonyl which is unsubstituted or substituted by fluorine, chlorine, bromine, nitro or methyl; phenylsulphonyl or naphthylsulphonyl which are unsubstituted or substituted by fluorine, chlorine, bromine, cyano, nitro, methyl, trifluoromethyl, $C_1-C_4$-alkoxy, $C_1-C_2$-fluoroalkoxy, $C_1-C_2$-chlorofluoroalkoxy or $C_1-C_4$-alkoxy-carbonyl; dimethyl(thio)phosphoryl; $C_1-C_4$-alkyl-$C_1-C_4$-alkoxy-(thio)-phosphoryl or di-($C_1-C_4$-alkoxy)-(thio)phosphoryl.

3. A substituted nitroalkene according to claim 1, in which
m represents the numbers 0, 1 or 2
A represents ethane-1,2-diyl,
$R^1$ represents pyridyl which is unsubstituted or substituted by fluorine; chlorine; bromine; cyano; nitro; $C_1-C_2$-alkyl which is unsubstituted or substituted by fluorine or chlorine; $C_1-C_2$-alkoxy which is unsubstituted or substituted by fluorine or chlorine; $C_1-C_2$-alkylsulphonyl which is unsubstituted or substituted by fluorine or chlorine
$R^2$ represents hydrogen,
$R^3$ represents hydrogen,
$R^4$ represents phenyl which is unsubstituted or substituted by fluorine; chlorine; $C_1-C_4$-alkyl; trifluoromethyl; $C_1-C_2$-alkoxy which is unsubstituted or substituted by fluorine or chlorine or $C_1-C_2$-alkoxy-carbonyl or naphthyl and
X represents sulphur or the group N—$R^5$, wherein,
$R^5$ represents hydrogen; methyl; ethyl; allyl; propargyl; formyl; $C_1-C_8$-alkyl-carbonyl; phenyl-carbonyl which is unsubstituted or substituted by fluorine or chlorine; $C_1-C_8$-alkoxy-carbonyl; benzyloxycarbonyl; phenoxy-carbonyl; benzyl which is unsubstituted or substituted by fluorine or chlorine or di-($C_1-C_2$-alkoxy)-(thio)phosphoryl.

4. A pesticidal composition comprising a pesticidally effective amount of at least one substituted nitroalkene according to claim 1 and a suitable carrier.

5. An insecticidal composition comprising an insecticidally effective amount of at least one substituted nitroalkylene according to claim 1 and a suitable carrier.

6. A method of combating pests comprising applying to said pests or to a habitat thereof a pesticidally effective amount of at least one substituted nitroalkene according to claim 1.

7. A method of combating insects comprising applying to said insects or to a habitat thereof an insecticidally effective amount of a substituted nitroalkene according to claim 1.

* * * * *